(12) United States Patent
Branch (10) Patent No.: US 6,669,660 B2
(45) Date of Patent: Dec. 30, 2003

(54) ORTHOTIC APPARATUS AND METHOD FOR USING SAME

(76) Inventor: Thomas P. Branch, 930 Lullwater Dr., Atlanta, GA (US) 30307

( * ) Notice: Subject to any disclaimer, the term of this patent is extended or adjusted under 35 U.S.C. 154(b) by 0 days.

(21) Appl. No.: 09/779,329

(22) Filed: Feb. 8, 2001

(65) Prior Publication Data

US 2001/0018565 A1 Aug. 30, 2001

Related U.S. Application Data (63) Continuation of application No. PCT/US99/18074, filed on Aug. 10, 1999.
(60) Provisional application No. 60/096,105, filed on Aug. 10, 1998, provisional application No. 60/096,104, filed on Aug. 10, 1998, and provisional application No. 60/095,952, filed on Aug. 10, 1998.

(51) Int. Cl.[7] .................................................. A61F 5/00
(52) U.S. Cl. .............................. 602/13; 602/5; 602/16; 602/20; 602/23
(58) Field of Search ............................... 602/5, 13, 12, 602/16, 19, 20, 21, 22, 23, 26, 62, 64, 10–11, 27, 40; 601/108–111; 128/845, 846, 882

(56) References Cited

U.S. PATENT DOCUMENTS

| | | | |
|---|---|---|---|
| 3,780,728 A | * | 12/1973 | Stader |
| 3,906,942 A |   | 9/1975  | Lumb, Jr. et al. |
| 3,937,215 A |   | 2/1976  | Barthlome |
| 4,146,021 A | * | 3/1979  | Brosseau et al. .............. 128/75 |
| 4,291,715 A |   | 9/1981  | Monte |
| 4,370,976 A |   | 2/1983  | Wanchik et al. |
| 4,599,996 A |   | 7/1986  | Seith et al. |
| 4,867,140 A |   | 9/1989  | Hovis et al. |
| 4,960,115 A | * | 10/1990 | Ranciato ....................... 602/23 |
| 5,020,515 A |   | 6/1991  | Mann et al. |
| 5,033,457 A |   | 7/1991  | Bonutti |
| 5,117,814 A |   | 6/1992  | Luttrell et al. |
| 5,219,324 A | * | 6/1993  | Hall ............................. 602/28 |
| 5,230,335 A | * | 7/1993  | Johnson, Jr. et al. ........ 607/104 |
| 5,242,378 A | * | 9/1993  | Baker .......................... 602/23 |
| 5,313,971 A |   | 5/1994  | Upshaw |
| 5,423,333 A | * | 6/1995  | Jensen et al. |
| 5,425,567 A | * | 6/1995  | Albecker, III |
| 5,445,602 A | * | 8/1995  | Grim et al. ................... 602/27 |
| 5,514,081 A | * | 5/1996  | Mann .......................... 602/20 |
| 5,514,155 A | * | 5/1996  | Daneshvar ................... 606/201 |
| 5,916,186 A | * | 6/1999  | Turto et al. .................. 602/20 |
| 5,950,628 A | * | 9/1999  | Dunfee ........................ 128/874 |
| 6,179,800 B1 | * | 1/2001 | Torrens ........................ 602/21 |

FOREIGN PATENT DOCUMENTS

| | | |
|---|---|---|
| DE | 92 17 225.3 | 4/1993 |
| WO | WO 99/03440 A1 | 1/1999 |

* cited by examiner

*Primary Examiner*—Nicholas D. Lucchesi
*Assistant Examiner*—Lalita M Hamilton
(74) *Attorney, Agent, or Firm*—Alston & Bird LLP (57) ABSTRACT

An inflatable bladder position a distance from a joint is attached to an external structural support which crosses the joint but does not support it. By inflating the bladder one limb segment is forced towards the external support thereby increasing the ranges of motion of that joint. Further, the inflatable bladder has an instant release valve which, when pressed, will instantly release the pressure within the bladder. The limb is positioned intermediate the bladder and the external structural support for optimal biomechanical efficiency.

44 Claims, 10 Drawing Sheets

ORTHOTIC APPARATUS AND METHOD FOR USING SAME

RELATED APPLICATIONS

This application is a continuation of prior application no. PCT/US99/18074, filed Aug. 10, 1999, which claimed priority of provisional patent application No. 60/096,105 filed Aug. 10, 1998; and provisional patent application No. 60/096,104 filed Aug. 10, 1998, and provisional patent application No. 60/095,952 filed Aug. 10, 1998. Thus the present application claims the full benefit and priority of all of said above-reverenced provisional and non-provisional applications.

TECHNICAL FIELD

This invention relates generally to orthotic devices and more particularly to orthotic devices designed to promote an increase in range of motion in a joint by the use of selectively inflatable and deflatable bladders.

BACKGROUND OF THE INVENTION

When a joint is injured either by trauma or by surgery scar tissue can form which prevents full range of motion of that joint. Obviously, this is a disadvantageous condition and should be corrected if possible. Often, such correction involves an attempt by the injured or those assisting the injured to gradually (often over a period of months) manipulate the joint so that full range of motion is eventually achieved.

Full range of motion of a joint depends upon the anatomy of that joint and on the particular genetics of each individual. Typically, joints move in two directions, flexion and extension. Typically, flexion is to bend the joint and extension is to straighten the joint; however, in the orthopedic convention some joints only flex. For example, the ankle has dorsiflexion and plantarflexion. Other joints not only flex and extend, they rotate. For example, the elbow joint has supination and pronation, which is rotation of the hand about the longitudinal axis of the forearm placing the palm up or the palm down.

There is a need for a class of orthotics which promote an increase in range of motion of the joint rather than to merely provide support. One such series of devices is called the Joint Active System, Inc. It combines a traditional orthotic with limb cuffs on each limb segment and a special hinge joint connecting the two cuffs. This special hinge joint has a ratchet system which allows the hinge to be sequentially bent or straightened with a special wrench or knob. If the cuffs are attached to each limb segment and the hinge is slowly bent then the joint is typically forced into flexion. Similarly, if the hinge is slowly straightened after being strapped on a bent joint, the joint is also straightened. This system relies upon the patient to strap a cuff on to each limb segment. This is difficult to do particularly if the joint to be treated is the arm needed to strap the brace. Furthermore, the pressure on each limb segment by each cuff is very painful as the joint is bent or straightened. Lastly, the ratchet system does not allow for instant release of the pressure used to force an increase in the range of motion.

Another series of devices is made by Dynasplint Inc. These devices are similar to the Joint Active System in that there is a cuff for each limb segment and a special hinge designed to promote an increase in range of motion. With the Dynasplint system, the hinge contains a special set of springs that, when tightened, will put a low load of pressure on the cuffs to bend or straighten. The same objections apply to the Dynasplint as they do to the Joint Active System. The cuffs are uncomfortable, the device is hard to put on and there is no instant release of the pressure. With this system the device must be worn for hours at a time to be effective.

There are other devices available which use inflatable bladders around a joint. They tend to use the bladder(s) to provide support across the joint. Such inflatable bladders are positioned across the joint or in near proximity to the joint.

Such conventional orthosis devices may be designed for support across a joint. In general an orthosis connects one limb segment to another across a joint. The connection is either a rigid member or a hinged joint. In this way orthotics work to support the joint as a means of protecting it. General reference is made to U.S. Pat. Nos. 5,542,911, 5,378,224, 5,348,530, and 5,730,710.

One particular device which uses the bladder(s) to provide support across the joint is also shown in U.S. Pat. No. 5,514,081 to Mann, which uses the inflatable bladder to cross the elbow joint to provide support for an elbow with a flexion contracture (the elbow joint can not fully extend). This device places the inflatable bladder across the joint so that when it inflates it holds the elbow in full extension. This device does not appear to include rigid structural members. Further, it does not isolate the bladder distant to the joint, thus maximizing the biomechanical forces across the joint for promoting elbow extension.

U.S. Pat. No. 3,581,740 has an air bladder which crosses multiple finger joints of a hand as well as the wrist. Upon inflation, the hand is moved to a normally extended, spaced apart, condition.

Some prior art patents use inflatable members to gain range of motion in the hand. U.S. Pat. No. 4,671,258 uses a cyclical therapeutic joint exerciser by inflating a pouch that crosses the joint and a spring steel insert that automatically bends the joint when the inflatable pouch is not inflated. U.S. Pat. No. 4,807,606 uses bladders around the joints in the hands to exercise the joints. That is to say, the bladders are inflated and deflated sequentially with a pump device to flex and extend hand joints.

U.S. Pat. No. 5,056,504 uses the inflatable bladder in the palm against a rigid structure to push the fingers into extension. However, this U.S. Pat. No. 5,056,504 includes a bladder which "crosses the joint", which is not only potentially painful to the user if the joint has undergone surgery, but is not optimally biomechanically efficient in the distribution of forces as will be described later with respect to applicant's invention.

Therefore, it may be seen that there is a need in the art to provide an improved orthotic device, which can be used to straighten ("orthoun" means to straighten) limbs or joints.

Therefore, it may be seen that there is a need in the art for an orthotic device and method of using same which provides optimal biomechanical distribution of load.

SUMMARY OF THE INVENTION

The present invention overcomes deficiencies in the prior art by providing an improved orthotic device. Generally described, the present invention comprises a strap, an inflatable member including an inflatable bladder, the inflatable member being spaced from the joint, and a device for inflating and deflating the inflatable member such that as the inflatable member is inflated, the strap is placed in increasing tension and the joint is moved.

More particularly described, the present invention comprises a structural body portion, an inflatable member, a flexible strap configured to be attached intermediate the structural body portion and the inflatable member, and an inflating device for inflating the inflatable member so that it increases in size, such that as the inflatable member is inflated, the inflatable member tend to push against the limb such that the limb is urged towards said structural body portion and the joint is moved. Other inventions are also included.

It is a further object of the present invention to provide an orthotic device which provides an optimal biomechanical application and distribution of load.

It is a further object of the present invention to provide an improved orthotic device which is easy to use.

It is a further object of the present invention to provide an improved orthotic device which is simple to manufacture.

It is a further object of the present invention to provide an improved orthotic device which applies no direct pressure on the joint itself.

It is a further object of the present invention to provide an improved orthotic device which is cost-effective to manufacture and use.

It is a further object of the present invention to provide an improved orthotic device which is efficient in its use of forces.

It is a further object of the present invention to provide an orthotic device which has increased reliability.

It is a further object of the present invention to provide an orthotic device which is easy to apply and remove.

It is a further object of the present invention to provide an orthotic device which allows for instant release of pressure.

It is a further object of the present invention to provide an orthotic device which provides a high load application It is a further object of the present invention to provide an orthotic device which provides an efficient load application.

It is a further object of the present invention to provide an orthotic device which applies comfortable pressure.

It is a further object of the present invention to provide an improved orthotic device which is light in weight and easy to transport.

It is a further object of the present invention to provide an improved orthotic device which can be used in conjunction with a crutch for structural support.

Other objects, features, and advantages of the present invention will become apparent upon reading the following detailed description of the preferred embodiment of the invention when taken in conjunction with the drawing and the appended claims.

DETAILED DESCRIPTION OF THE PREFERRED EMBODIMENT

Reference is now made to the Figures, in which like elements indicate like elements throughout the several views.

The application will be discussed by reference to several different embodiments, which may share inventive concepts or alternately may each include individual inventive concepts.

First Embodiment, FIGS. 1–4

Figure 1:
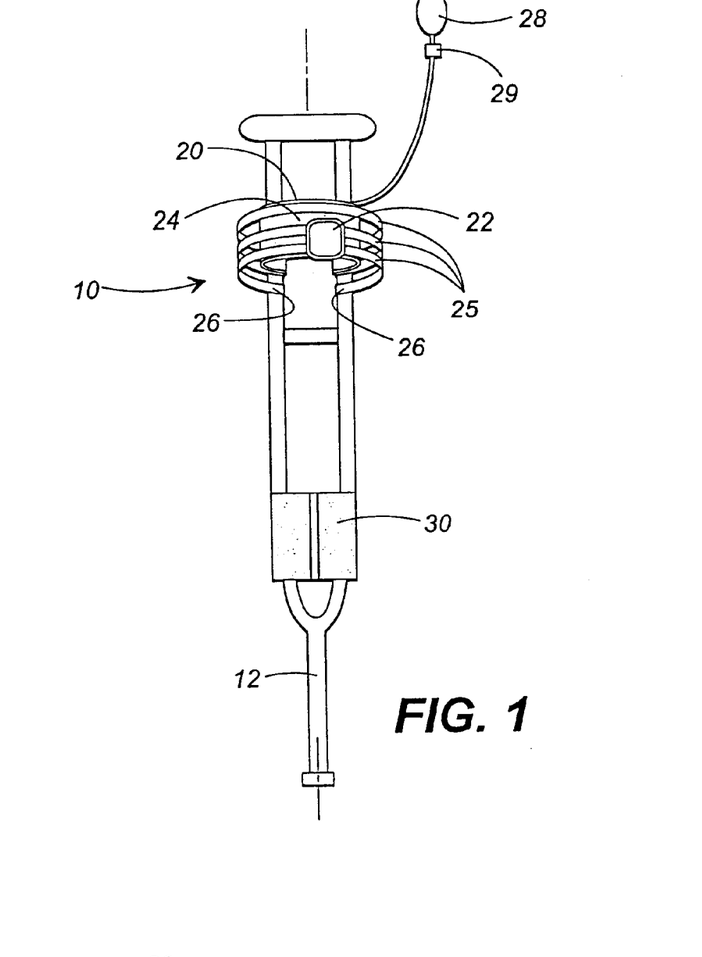
FIG. 1 is a front view of a knee extension assembly 10 and ankle support member 30 used in conjunction with a conventional crutch 12.
Figure 2:
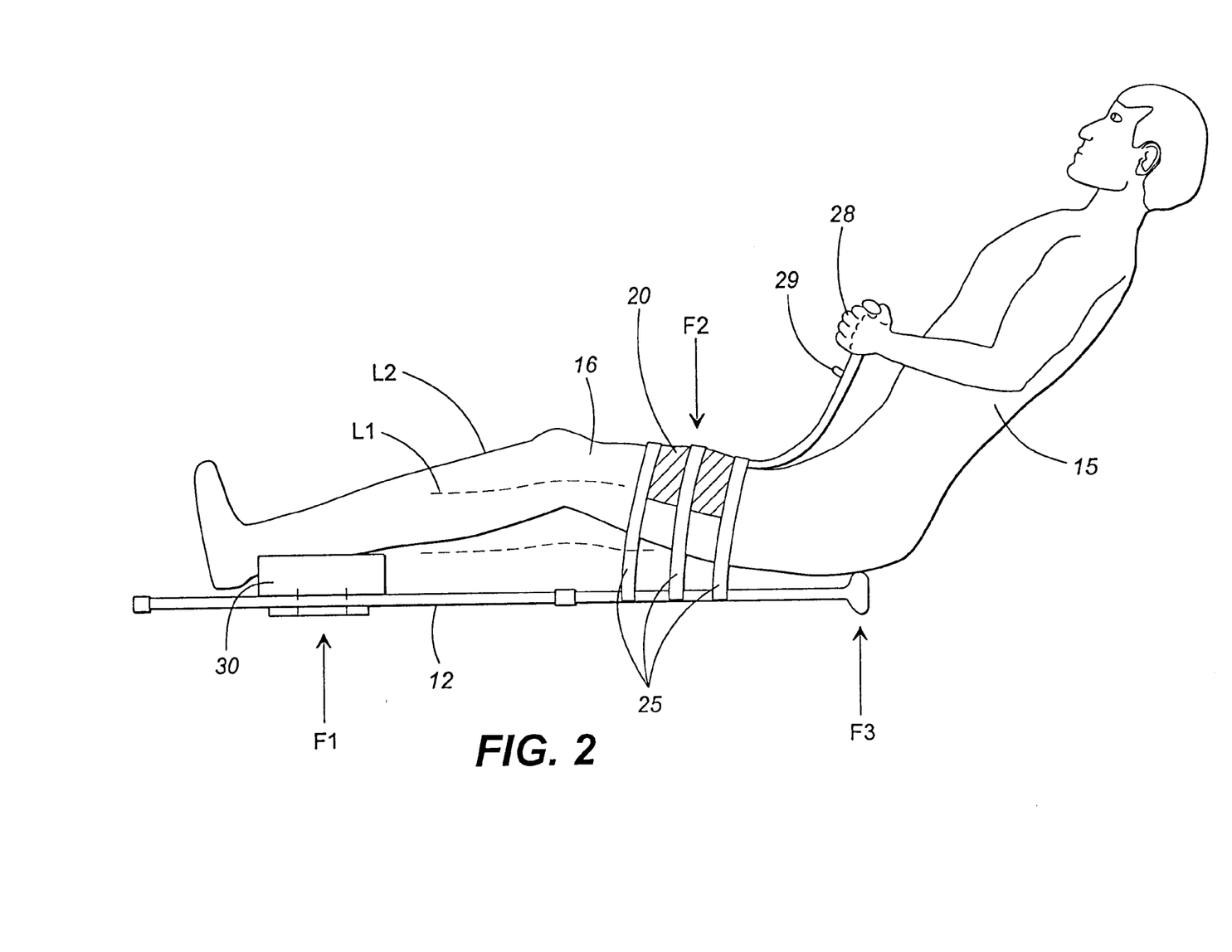
FIG. 2 is a is a side view of the elements 10, 12, being used by a wearer 15.
Figure 3:
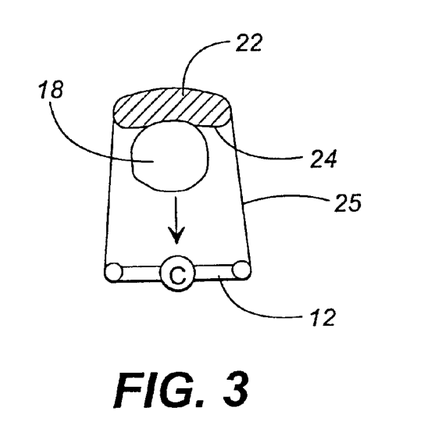
FIG. 3 is a top cross-sectional view taken transverse to the longitudinal axis of the crutch and the wearer's leg of FIG. 2, with the cross-section taken through the inflatable air bladder 22 and its containing pouch 24.
Figure 4:
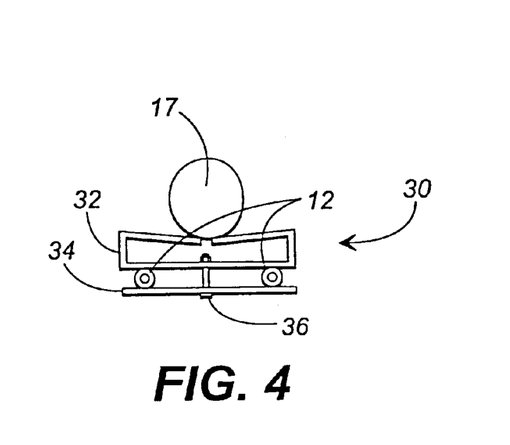
FIG. 4 is another transverse cross-section taken from the FIG. 1 configuration, but this time the cross-section is taken just above the ankle support member 30.

FIG. 1 is a front view of a knee extension assembly 10 and an ankle support member 30 used in conjunction with a conventional crutch 12. FIG. 2 is a is a side view of the elements 10, 12, 30 being used by a wearer 15. FIG. 3 is a top cross-sectional view taken transverse to the longitudinal axis of the crutch and the wearer's leg of FIG. 2, with the cross-section taken through the inflatable air bladder. FIG. 4 is another transverse cross-section taken from the FIG. 1 configuration, but this time the cross-section is taken just above the ankle support member 30.

The crutch as shown in FIG. 1 is a conventional type of crutch, which is a distinctive aspect of the present invention in that conventional crutches are readily available within the market. The present invention particularly adds the use of a knee extension assembly 10 and an ankle support member 30.

The knee extension assembly 10 includes an inflatable member 20, a plurality of straps 25, and a conventional hand-operated pump 24 with a bleed valve 29. The inflatable member 20 can include an inflatable bladder 22 contained within a fabric pouch 24. The inflatable bladder 22 can, as in other configurations described herein, may be inflated by the conventional hand-operated pump 24 and deflated by use of the bleed valve 29. The plurality of straps 25 as shown in FIG. 2 can position the leg between the inflatable member and the crutch, while containing and attaching the inflatable member relative to the crutch. The configuration shown in FIGS. 1–2 includes three straps. However, other strap or bladder configurations may be used as known in the art.

The ankle support member 30 includes a cradle portion 32 and a back portion 34 is attached to the crutch towards the lower end of the crutch by use of conventional fasteners such as 36, although any suitable attachment of the ankle support member 30 to the crutch is suitable. The cradle portion 32 defines a generally upwardly (as FIG. 4 is viewed) cradle which is configured to accept a length of the leg of the user.

Upon inflation of the inflatable member inflatable member 20, it may be understood that a "three point" force combination is provided which allows for effective extension of the knee by use of an optimal, highly efficient but comfortable biomechanical application of load. This three point contact configuration is illustrated in FIG. 2 by the force arrows "F1", "F2", and "F3". Force arrow "F1" illustrates force provided upwardly on the leg by the ankle support member 30. The force arrow "F2" illustrates force provided downwardly on the leg atop the thigh of the leg by the inflatable member 20 of the knee extension assembly 10. It may be understood that this force is translated to the crutch through tension in the straps 25. The force arrow "F3" illustrates force provided upwardly on the leg by the upper end of the crutch (which may be the padded underarm rest). This three point action is further described elsewhere in this application with reference to FIG. 19.

It should be understood that although FIG. 2 illustrates the use of the air bladder atop the thigh, alternate locations of the air bladder are likewise contemplated; the inflatable bladder could alternatively be placed upon the knee, or the tibia. However, the present invention contemplates adjustability of the location of the knee extension assembly 10 along the length of the crutch, as at times (for example at the beginning of treatment) the knee joint may be sensitive to contact, and thus the knee extension assembly 10 may be adjusted so it is atop the thigh. At the same time, biomechanically the knee is a desirable location for application of the load, so later in treatment, when the knee is not as tender, the knee extension assembly 10 may be adjusted so it is atop or at least closely adjacent the knee.

Under one configuration of the present invention, the ankle support member 30 will remain at least temporarily attached to the crutch during its normal use. The patient can use the crutch in the conventional manner, with the assembly 10 carried therewith on the crutch if so desired. When an orthotic session is desired, the patient will then typically sit on a chair with the upper (underarm) portion of the crutch positioned beneath the relevant buttock. The remainder of the elongate crutch is positioned relatively underneath the length of the patient's leg, with the ankle support member 30 portion being positioned under the patient's ankle. The device 10 is then attached to its position as shown in FIG. 2, and the adjustable straps are adjusted to a comfortable tension. The bladder is then filled as desired, with pressure relief being available as desired.

The straps are adjusted to provide some initial amount of pressure, with the final amount of pressure and resulting force being provided by the air. It should also be understood that the adjustability of the straps accommodates various knee positions; it should be understood that during the initial stages of recovery, the leg may not be able to be bent very much at the knee, whereas towards the end of the recovery period, the leg preferably may be bent substantially straight at the knee.

It should be understood that one portion of the present invention includes the use of straps including hook-and-loop (such as VELCRO) attachment which allow for a "take-up" feature; this feature allows for the combination of large motions of the limb. However, other take-up configurations may be used such as known in the art, such as friction or other buckles, without departing from the spirit and scope of the present invention. This applies throughout this discussion.

As noted above, the knee extension assembly according to the present invention is contemplated for use in conjunction with a conventional crutch member such as known in the art and conventionally available. It should be understood that such a crutch configuration could also be a special crutch specially configured to work with the orthotic device according to the present invention, or could simply be a straight board or other elongate structural member.

Figure 5:
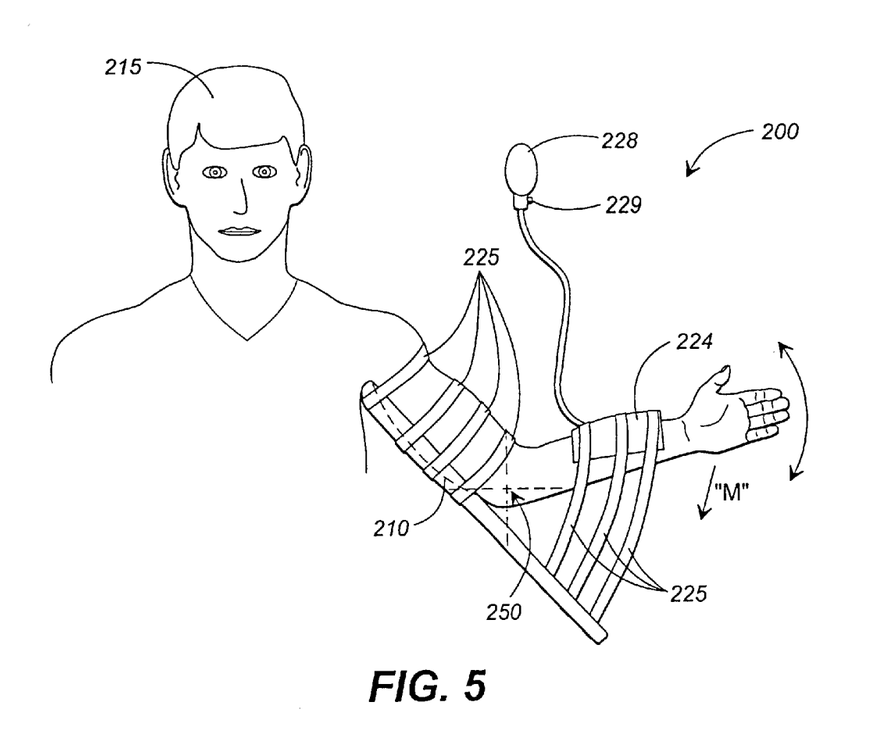
FIG. 5 shows a front view of a second embodiment 200 of the invention, being an arm orthotic device.

Second Embodiment—FIG. 5

FIG. 5 illustrates the use of a rigid plastic or other suitable material, to provide an elongate structural member 210 which may be attached to the underside of the arm, with its lower end extending beyond the elbow, terminating in a "free end". Approximate this "free end" are attached three (as shown) straps 225 which connect an inflatable member 220 (an air bladder in a fabric pouch) to the free end of the elongate member. This member 220 is configured to be positioned adjacent to the forearm of a wearer, such that inflation of the air bag therein tends to provide pressure causing movement such as shown as M. This is conventionally called "extension" and is desired in certain types of orthotics.

It should be understood that this FIG. 5 configuration includes the "three point" force combination as described above. However, this FIG. 5 configuration is similar to the FIGS. 6 and 7 configuration, and the "three point" force configuration will be described in more detail in reference to FIG. 6.

Figure 6:
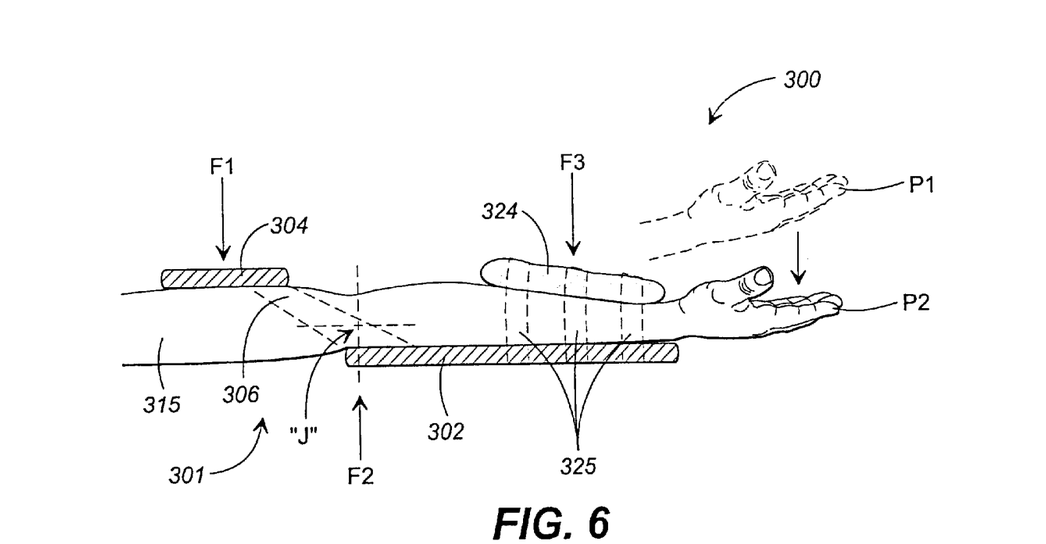
FIG. 6 is a side view of a third embodiment 300 of the present invention, being an orthotic device for extending the forearm relative to the upper arm from position P1 to position P2.
Figure 7:
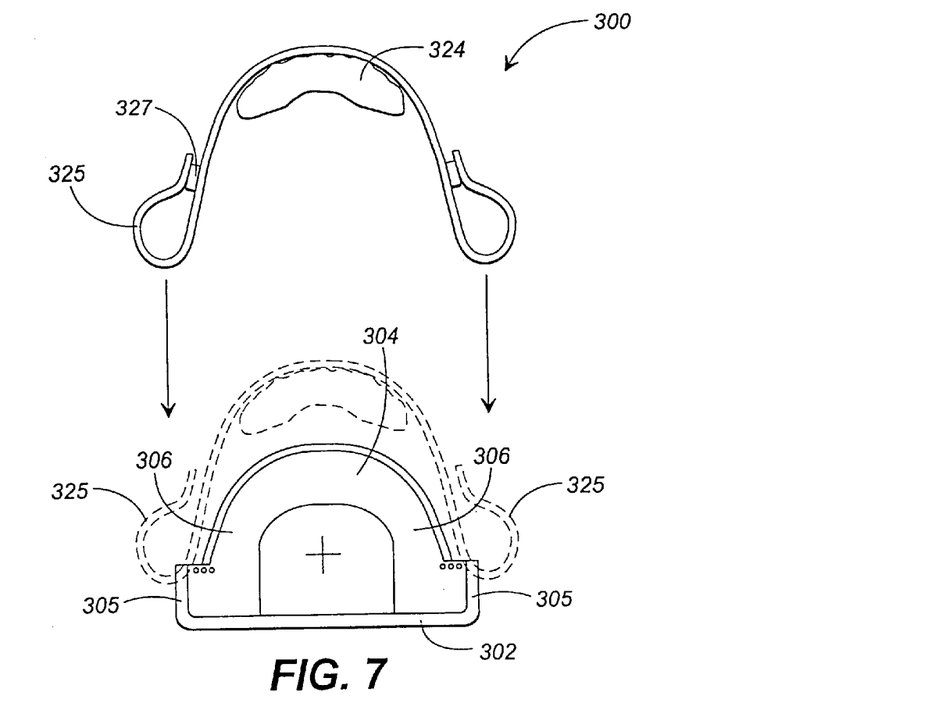
FIG. 7 is an exploded, illustrative, view of the device 300 of FIG. 7, with the portion comprised of the straps 325 and the inflatable member 324 (which includes an air bladder within a fabric pouch) detached from the main body of the device 300.

Third Embodiment—FIGS. 6 and 7

FIGS. 6 and 7 show a third embodiment of the present invention, being an apparatus 300 configured to be attached to the arm of a wearer 315. It should be understood that FIG. 6 is a more simplified version.

The apparatus 300 includes a substantially rigid structural frame 301 including a forearm bearing portion 302 and an upper arm bearing portion 304, connected by one or more connecting members 306. Also included are straps 325 and an inflatable member 320, which can include an inflatable bladder contained by a fabric pouch. As are other configurations discussed herein, the straps are sewn to the fabric pouch by conventional means. As elsewhere in this discussion VELCRO-type attachments at 327 may be provided for detachability and adjustability of the straps.

Flanges 305 (see FIG. 7) may be optionally used if desired to extend upwardly on either side of the main body to contain the forearm as desired.

FIG. 7 shows the embodiment in slightly more detail than FIG. 6. In FIG. 7, the forearm bearing portion 302, the upper arm bearing portion 304, and two connecting members 306 are shown; it may be understood that in the FIG. 7 version shown they are all part of an essentially one-piece frame which in the preferred embodiment is plastic. It should be understood that the upper arm bearing portion is contoured to conform somewhat to the upper surface of the upper arm for comfort purposes when bearing downwardly thereon.

The frame 301 of the apparatus can be plastic, wood, metal, a metal/fabric sling, or other material(s) suitable to provide the needed structural support. It should be understood that the members 302 and 305 of the frame 301 could be rigidly attached together by virtue of being part of an integral, one-piece unit, or alternately could be part of a multiple-part device which allows for relative adjustment between the members 302, 304 as desired.

As shown in FIG. 6, it may be seen that the "three point" force configuration is again utilized in this embodiment, as shown by force arrows "F1", "F2" and "F3". Force arrow "F3" illustrates the force down by the inflatable member. Force arrow "F2" illustrates the force up by forearm bearing portion 302. Force arrow "F1" illustrates the force down by upper arm bearing portion 304.

It should be understood that during the initial stages of recovery, the elbow may not be able to accommodate much pressure, and for that reason the elbow may be placed off the forearm bearing portion 302. However, towards the end of the recovery period, the elbow may be placed on the forearm bearing portion 302 for optimal biomechanical application of force.

Figure 8:
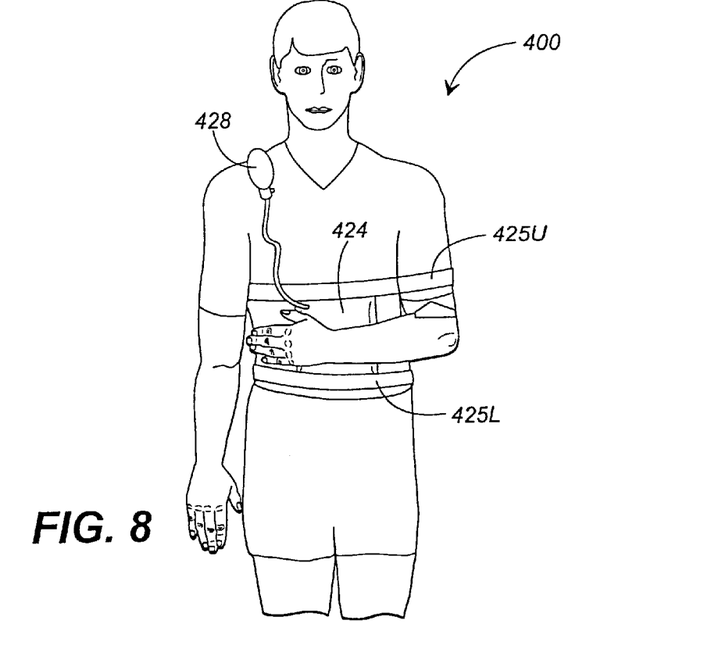
FIG. 8 is a front view of a fourth embodiment of the invention, being an apparatus 400 used in conjunction with a user 415, to provide external rotation of the shoulder.
Figures 9, 10, 11:
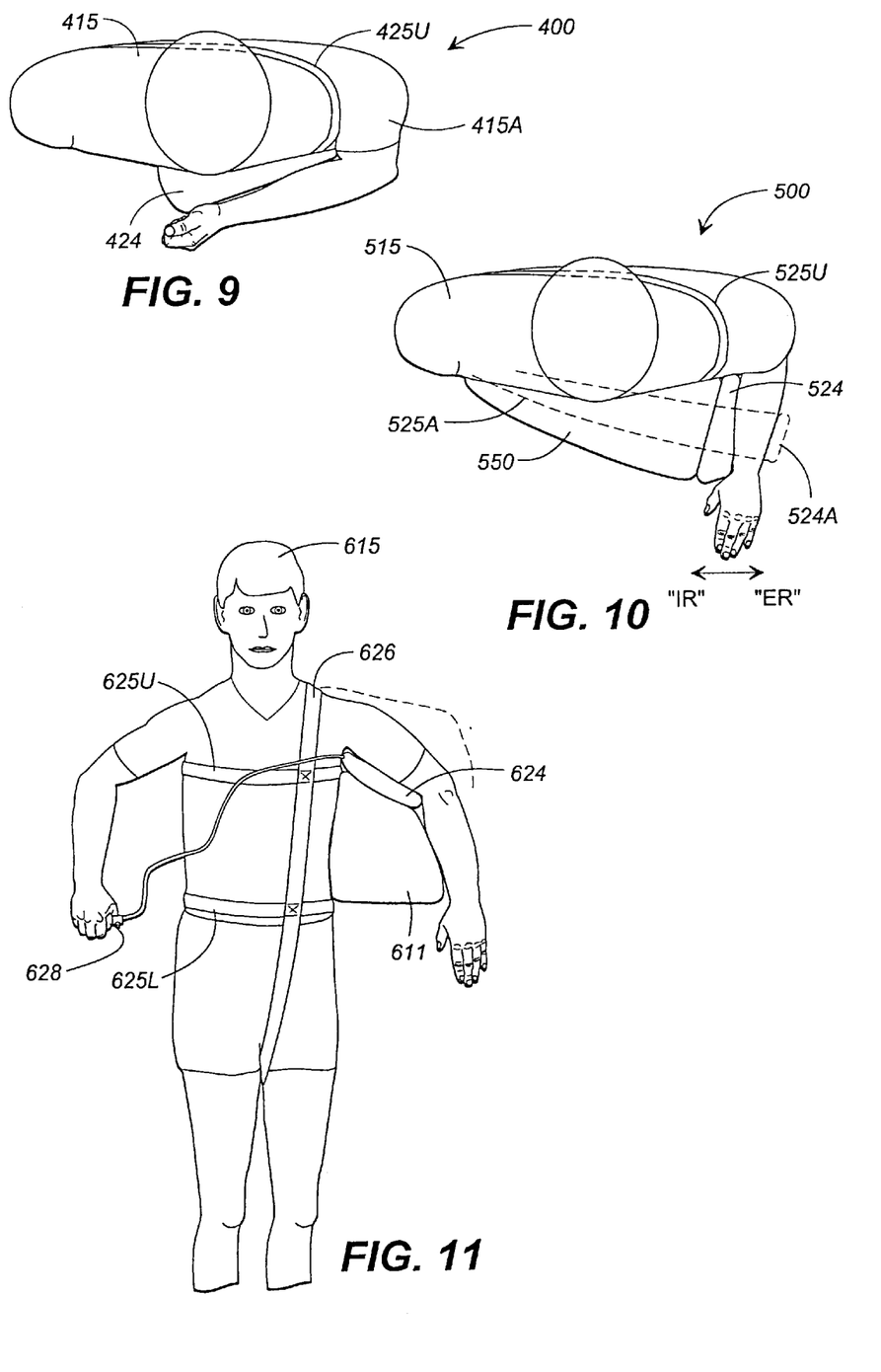
FIG. 9 is a top view of some of the elements of FIG. 8.
FIG. 10 is a top view of a fifth embodiment of the present invention, being a device 500 which provides external rotation of the shoulder in a different range.
FIG. 11 is a front view of a sixth embodiment of the present invention, being a device 600 which provides abduction of the shoulder.

Fourth Embodiment—FIGS. 8 and 9

FIGS. 8 and 9 show an apparatus 400 which may not include any substantially rigid members (although one against the stomach may be used), but includes the use of an inflatable member 424 and a pair of straps 425U, 425L (upper and lower), together which are configured to provide external rotation of the shoulder. The upper strap 425U may be passed around the upper torso and arm of a user, leaving the opposite arm free. The lower strap 425L may be provided around the lower torso of the wearer, such as would a conventional belt. Between the upper and lower straps are attached an inflatable member 424 (being a bladder within a pouch), having its upper edge attached to the upper strap, and its lower edge attached to the lower strap, with the air bladder therein configured to be inflated and deflated as noted before.

To utilize the apparatus, the forearm is placed adjacent the air bladder, and the upper strap 425U is provided in a suitably taut configuration to keep the relevant upper arm against the wearer's side for optimal biomechanical effect. The air bladder is then inflated, causing external rotation of the shoulder. As may be understood, when desired, the air bladder may be deflated as needed, in order to remove the device, or in order to alleviate pain.

It should be understood that other configurations are also contemplated for maintaining the upper arm against the side of the user, such as but not limited to a cuff (not shown) to contain the arm but allow it to rotate as it is strapped to the body.

Fifth Embodiment—FIG. 10

As shown in FIG. 10, the two-strap apparatus as shown in FIG. 7 may be complimented with a foam block or wedge 550 to provide a range of motion of external rotation which is different from the range of motion provided in the apparatus shown in FIGS. 8 and 9.

In this configuration, the forearm is oriented generally forwardly, and along the conventional line of sight of the user/patient 515, and the inflatable member 524 is located between the foam member and the forearm. It should also be noted that the foam block 550 could be a separate air bag 550, which could be inflated to a desired size and temporarily sealed.

Internal rotation could further be provided, by use of additional straps 525A and an additional inflatable air member 524A (shown in dotted line) to provide movement towards the body. These straps 524A would have one of their ends attached to the air bladder, and their other ends attached relative to the patient's body, preferably at about the right shoulder.

Therefore, internal and external rotation could be provided by the use of a pair of bladders as desired "IR" and "ER".

It should be understood that the configurations described above which include the two oppositely located bladders may be used to provide "CPM", otherwise known as continuous passive motion.

Sixth Embodiment—FIG. 11

FIG. 11 illustrates a sixth embodiment 600 of the present invention, including a pair of horizontally-oriented straps 625U, 624L, an upper strap 624U located about the upper torso and approximate the armpit region, and the lower strap 625L being strapped about the lower torso of the body slightly upwardly of the belt region. Between the two straps is supported a foam pad, which fits generally underneath the armpit region of a particular arm of the wearer 615. An inflatable member 624 is located intermediate the underneath of the upper arm and the foam pad, such that inflation of the air bladder by the air pump 628 by the wearer 615 causes abduction of the shoulder. Although not shown, it should also be understood that a second inflatable member (not shown), with accompanying straps, could be used to cause movement in the opposite direction. A third shoulder-to-crotch strap 626 extends to underneath the groin region could also be used in order to provide support for pulling the scapula downwardly. This isolates motion to the glenohumeral joint (otherwise known as the arm/shoulder blade joint) as opposed to the acronmioclavicular joint.

Figure 12:
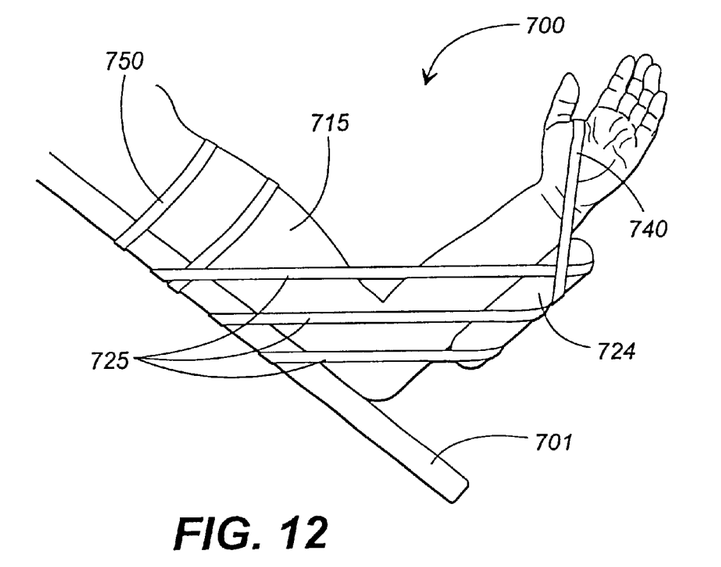
FIG. 12 is a side view of a seventh embodiment of the present invention, being a device 700 for flexion of the elbow.

Seventh Embodiment—FIG. 12

This embodiment of the invention comprises a device 700 which uses a substantially rigid structural member 701, an inflatable member 724, and straps 725 which connect the structural member 701 to the inflatable member 724. An additional hand strap 740 is provided to discourage movement of the inflatable member from its shown position to a position more towards the elbow. Another set of conventional straps such as 750 may be used to attach the structural member 701 relative to the upper arm.

As may be understood, by inflating the inflatable member 724, the straps 725 are drawn into tension and flexion of the elbow joint is provided.

Figure 13:
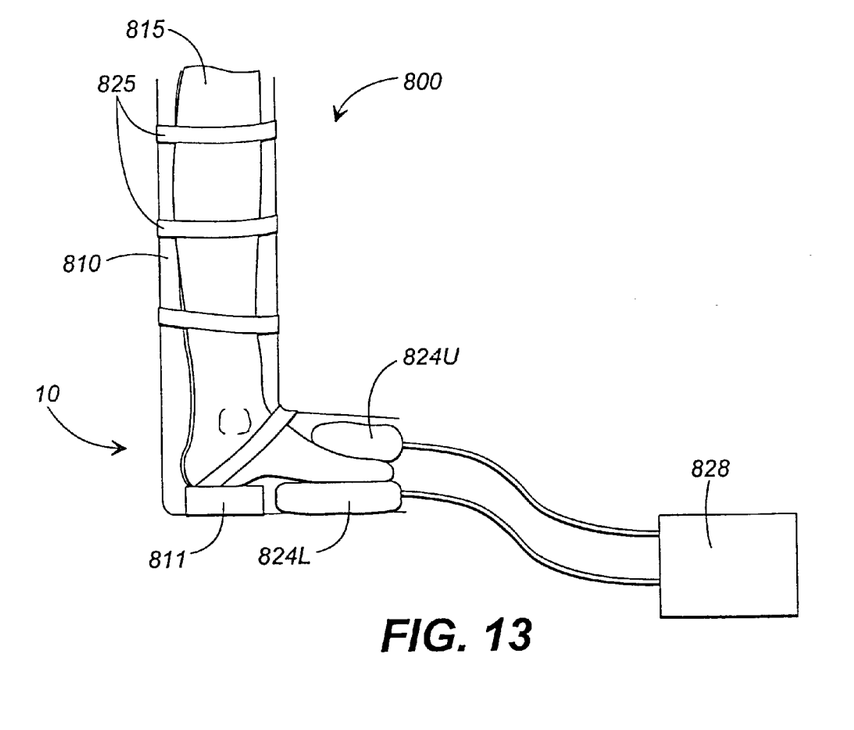
FIG. 13 is a side view of an eighth embodiment of the present invention, being a device 800 which promotes both dorsiflexion and plantarflexion alternately and continuously.

Eighth Embodiment—FIG. 13

FIG. 13 relates the use a orthotic device 800 which include the use of alternating air flow to respective air bladders to cause range of motion in, for example, an ankle. This is referred to as providing "continuous passive motion".

The device includes a hard shell boot 810, within which the lower leg, ankle, and foot of a patient is inserted. Two air bladders 824U, 824L, (although additional bladders could be used), are included within the boot. One air bladder is located above the foot proximate the toe area, whereas the other air bladder is located beneath the sole of the foot proximate the toe area. The "upper" bladder 824U is separate from the "lower" bladder 824L, and the upper and lower bladders can be inflated and deflated separately, in order to provide an up and down motion of the foot, translating into an up and down motion of the ankle.

At least two types of flexion are intended to be provided under the present invention. These two types of flexion are plantarflexion, and the other type is dorsiflexion.

In an alternate embodiment of the present invention, two hinged flaps are also used within the boot cavity, one atop the foot and below the upper bladder, and the other below the foot and above the lower bladder. These two flaps correspond to the two bladders, such that inflation of the lower bladder pushes upwardly on the lower pivoting flap, causing upper flexion (dorsi) flexion, and increased air within the upper bladder, creates downward movement of the upper flap, causing the opposite type of flexion.

The two bladders are connected by two corresponding air lines, each of which are attached at their opposite ends to a common air source. Under one configuration of the present invention, the lines are alternatively filled and evacuated, causing the dual motion desired under the present invention.

Figure 14:
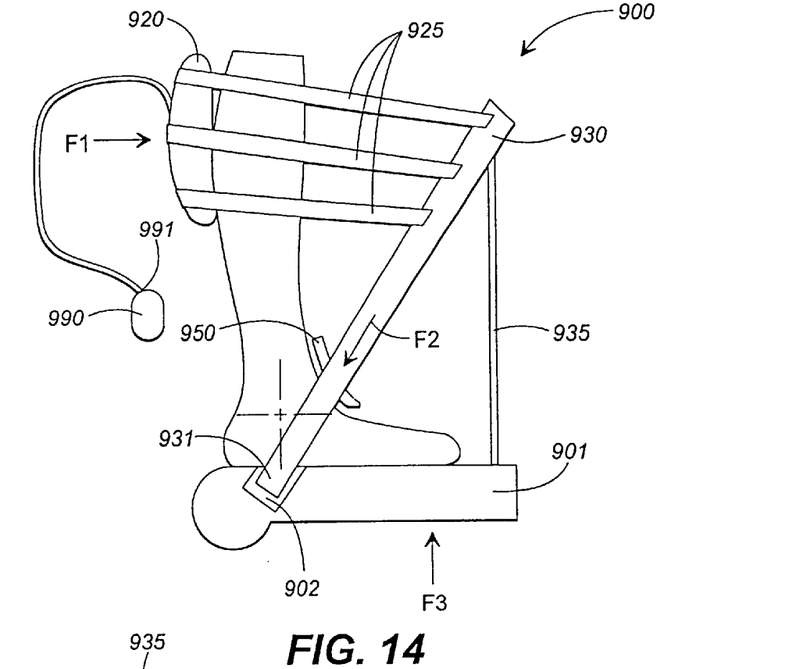
FIG. 14 is a side view of a ninth embodiment of the present invention, being a device 900 which provides dorsiflexion of the ankle joint by capturing the foot and using the inflatable member to pull the ankle into dorsiflexion. This apparatus 900 includes a substantially flat base 901, an inflatable member 920, and an including floating yoke member 930 which captures the foot as described in further detail below.
Figure 15:
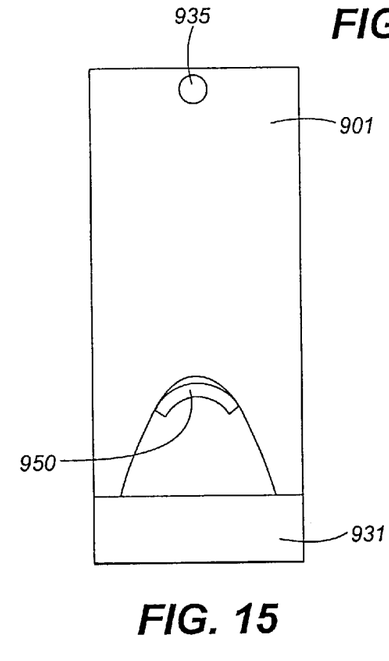
FIGS. 15 and 16 are rear elevational and top plan views, respectively, of portions of the device of FIG. 14.
Figure 16:
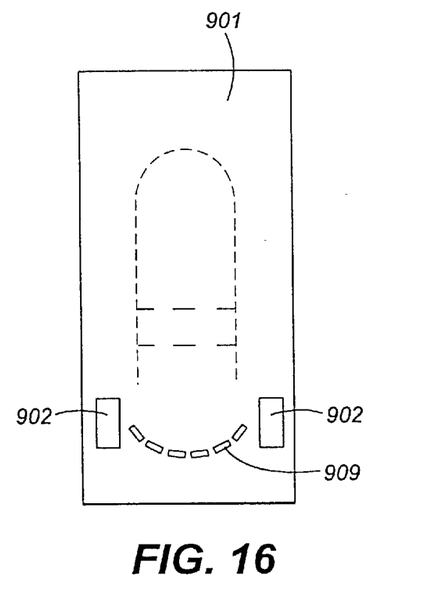

Ninth Embodiment—FIGS. 14–16

This apparatus 900 includes a substantially flat base 901, an inflatable member 920, and a floating yoke member 930. The substantially flat base 901 includes a pair of upwardly-directed holes 902 (as FIG. 14 is viewed) which slidably accept a corresponding pair of downwardly-directed feet 911 which extend downwardly and leftwardly at an incline from the inclined yoke plate 910.

Straps 925 are attached intermediate the upper end of the inclined yoke plate 910 and the inflatable member 920. A vertical anchor strap 935 is connected intermediate the upper end of the inclined yoke plate 910 and the base plate 901.

The inclined yoke plate 910 includes a tonguelike pad at 950 to provide a cushion as described below for the upper side of the foot. The tonguelike pad at 950 is located at the top of the yoke and can act as a type of "tramoline" pushing on the dorsum of the foot with a cushioning effect.

An air pump 990 with a quick release valve 991 is also included to inflate and deflate the air bladder within the fabric pouch of the inflatable member 920.

Such a yoke concept accommodates different sized feet, as a variety of feet can be slipped into the gap defined by angled yoke plate.

After the straps are properly adjusted to take out slack, the air pump 990 is used to inflate the inflatable member 920, tensioning the straps and providing a force on the calf of the leg of the wearer. This causes the ankle into desired dorsiflexion.

The downwardly-directed feet 931 do not bottom out in the holes 902, but instead are allowed to slide or "float" upwardly and downwardly therein. Since the straps are in tension, it may be understood that a force is applied to the top of the foot by the angled yoke plate 930 at the location of the tonguelike pad at 950. This causes the foot to be maintained in place due to pressure of the yoke atop the foot, instead of allowing the heel of the foot to lift from its location atop the base plate 901. A heel cup or stop 909 also may be used as shown in dotted line in FIG. 16.

The spherically shaped member 950 is configured to allow the base plate 901 to be put on a level supporting surface such as a floor surface such that the spherically shaped member 950 can provide a rolling pivot or rocking point about which the base plate 901 can rotate. This conveniently allows the lower leg to be maintained in a substantially consistent orientation while the forces within the apparatus cause the ankle of the foot into desired dorsiflexion. This can be quite convenient as it allows the user/patient to sit comfortably while undergoing the process.

Figure 17:
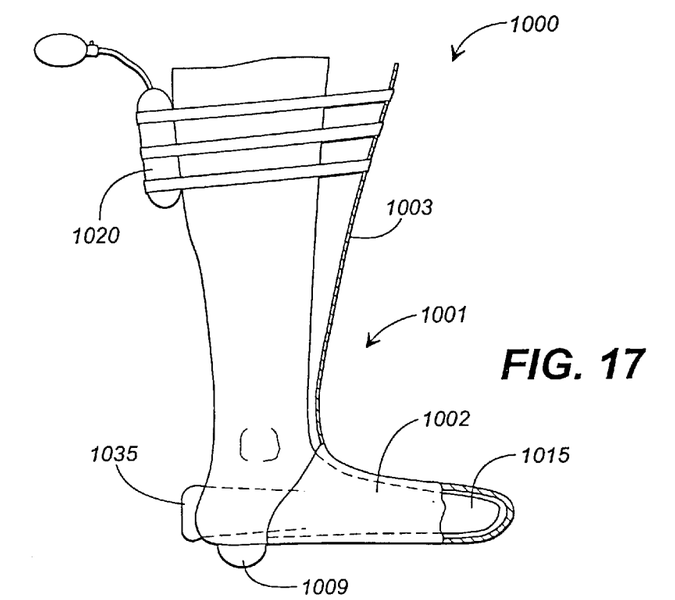
FIG. 17 is a side view of a tenth embodiment of the present invention, being a device 1000 which provides dorsiflexion of the ankle joint by capturing the foot and using the inflatable member 1020 to pull the ankle into dorsiflexion. This device 1000 includes a substantially rigid structural member 1001 which resembles a open-backed "slipper" portion 1002 with a front vertical flange 1003 which extends upwardly from the top of the slipper portion and along the front of the shin of the wearer 1015.

Tenth Embodiment—FIG. 17

This device 1000 includes a substantially rigid structural member 1001 which resembles a open-backed "slipper" portion 1002 with a front vertical flange 1003 which extends upwardly from the top of the slipper portion and along the front of the shin of the wearer 1015. The wearer's front foot may be placed in the cavity of the slipper portion 1002, and an inflatable member 1020 may be placed behind the calf. This inflatable member is attached relative to the upper, free, end of the front vertical flange 1003 by one or more straps 1025.

After initial adjustment of the straps 1025, the inflatable member may be inflated by use of the air pump, causing the straps to be drawn into tension, and the calf to be pulled forward. This causes desired dorsiflexion of the ankle.

An optional strap at 1035 may be used to maintain the foot in place.

The spherically shaped member 1009 of the substantially rigid structural member 1001 is configured to allow the substantially rigid structural member 1001 to be put on a level supporting surface such as a floor surface such that the spherically shaped member 1009 can provide a rolling pivot or rocking point about which the substantially rigid structural member 1001 can rotate. This conveniently allows the lower leg to be maintained in a substantially consistent orientation while the forces within the apparatus cause the ankle of the foot into desired dorsiflexion. As noted above this can be quite convenient as it allows the user/patient to sit comfortably while undergoing the process.

It should be understood that this configuration 1000 may be used instead or in combination with the FIG. 14 configuration, if the yoke of FIG. 14 applies too much pressure.

Figure 18:
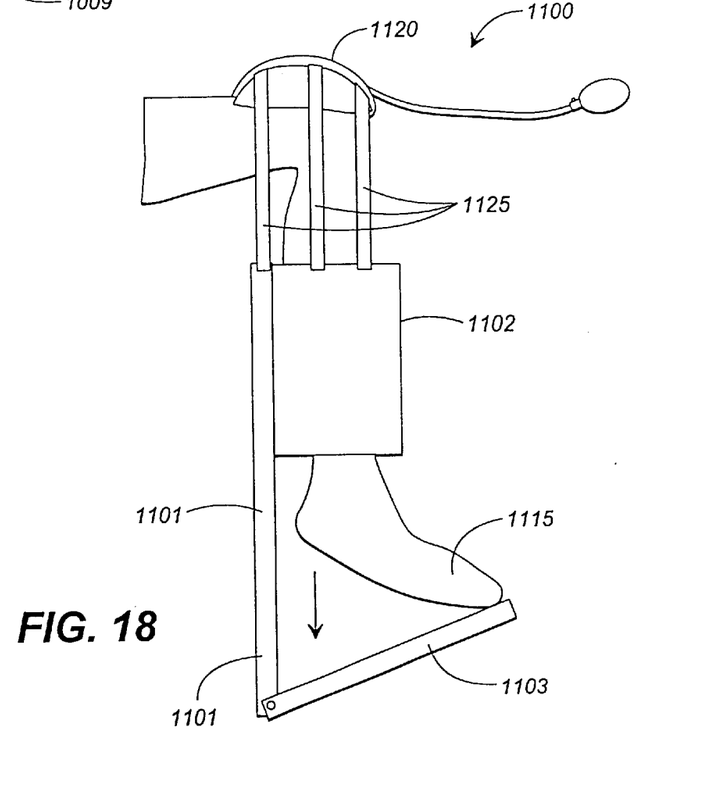
FIG. 18 is a side view of an eleventh embodiment of the present invention, being another orthotic device 1100 which can be used to provide dorsiflexion of the ankle. This device 1100 includes a base 1101, a cuff 1102 fixed to the base, a selectively positionable foot plate 1103, an inflatable member 1120, and connecting straps 1125.

Eleventh Embodiment—FIG. 18

FIG. 18 shows another orthotic device 1100 which can be used to provide dorsiflexion of the ankle. This device 1100 includes a base 1101, a cuff 1102 fixed to the base, a selectively positionable foot plate 1103, an inflatable member 1120, and connecting straps 1125.

The selectively positionable foot plate 1102 is mounted to the base 1101 via a pivotable connection as known in the art, which allows for initial adjustment. However, it should be understood that when the orthotic device 1100 is in use, the pivoting connection is fixed such that the foot plate 1103 is fixed relative to the base 1101.

The cuff 1102 is fixed to the base, and allows for the lower leg of the wearer 1115 to slide therein as described below.

After initial adjustment of the foot plate 1102 and the straps 1125, the inflatable member 1125 is inflated, causing the straps to be drawn into tension. The inflatable member 1125 pushes down on the leg, namely the anterior aspect of the distal thigh, with the kneed flexed approximately 90 degrees. This causes the lower leg to move downwardly while being contained by the cuff 1102. This forces the ankle into dorsiflexion as the foot of the wearer bears against the foot plate 1103. Pressure may be relieved as desired.

Figure 19:
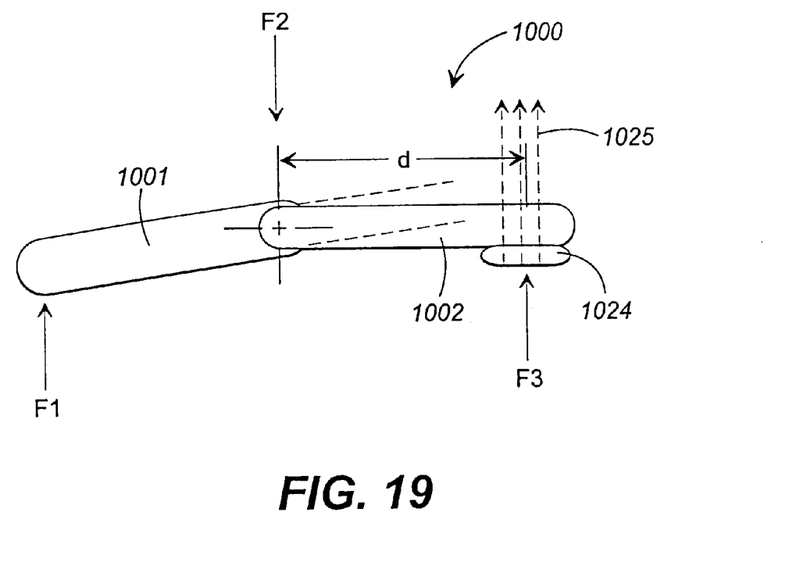
FIG. 19 is an illustrative view 1200 of a pair of exemplary limb members (such as an upper and lower leg, or such as an upper and lower arm), and how such members can be captured by the "three point" force configuration described above. Such an inventive configuration provides an optimally efficient biomechanical application of force by positioning the inflatable member as far as possible from the pivoting point, whether that pivoting point be the joint (as shown in the FIG. 6), or the interface between the limb and the structural member (see FIG. 2).

FIG. 19

FIG. 19 is an illustrative view 1200 of a pair of exemplary limb members (such as an upper and lower leg, or such as an upper and lower arm), and how such members can be captured by the "three point" force configuration described above. Such a configuration provides an optimally efficient biomechanical application of force by positioning the inflatable member as far as possible from the pivoting point, whether that pivoting point be the joint (as shown in the FIG. 6), or the interface between the limb and the structural member (see FIG. 2).

Such a combination of the "three point" force configuration, the inflatable member, tensioning straps, and structural member is submitted to be a significant improvement over the prior art as pressure is not provided across the joint, as might be provided by a simple "wrap" or the known cited art.

Figure 20:
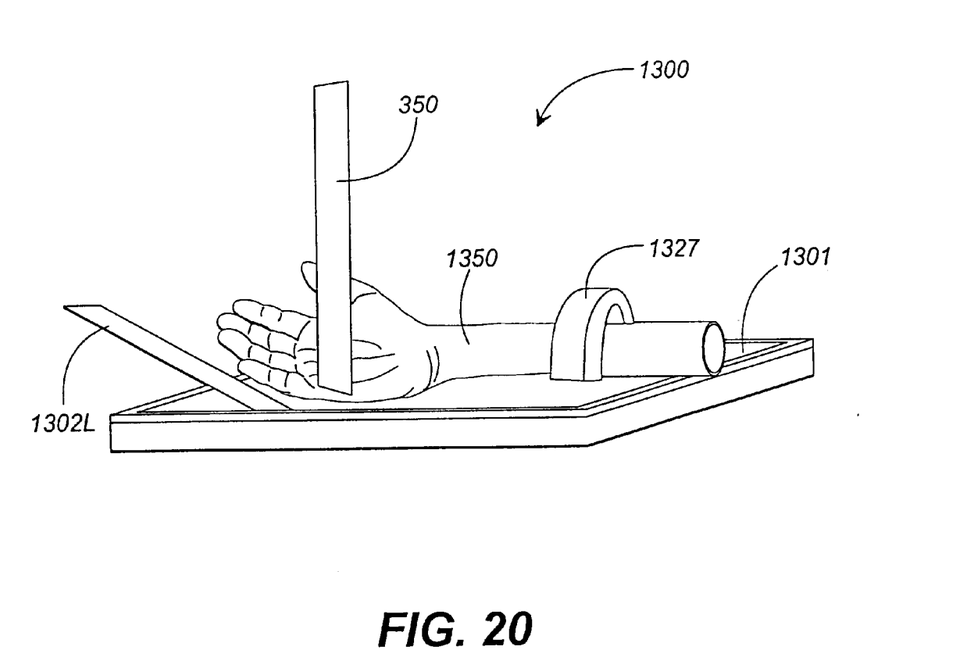
FIGS. 20 and 21 are pictorial and end views, respectively, of a forearm supination and pronation device 1300 which includes a base 1301, right and left adjustable base flanges 1302L, 1302R, respectively, an inflatable member 1320, straps 1325, a retaining cuff 1327, and a glove assembly 1350 including a thumb retainer 1351.
Figure 21:
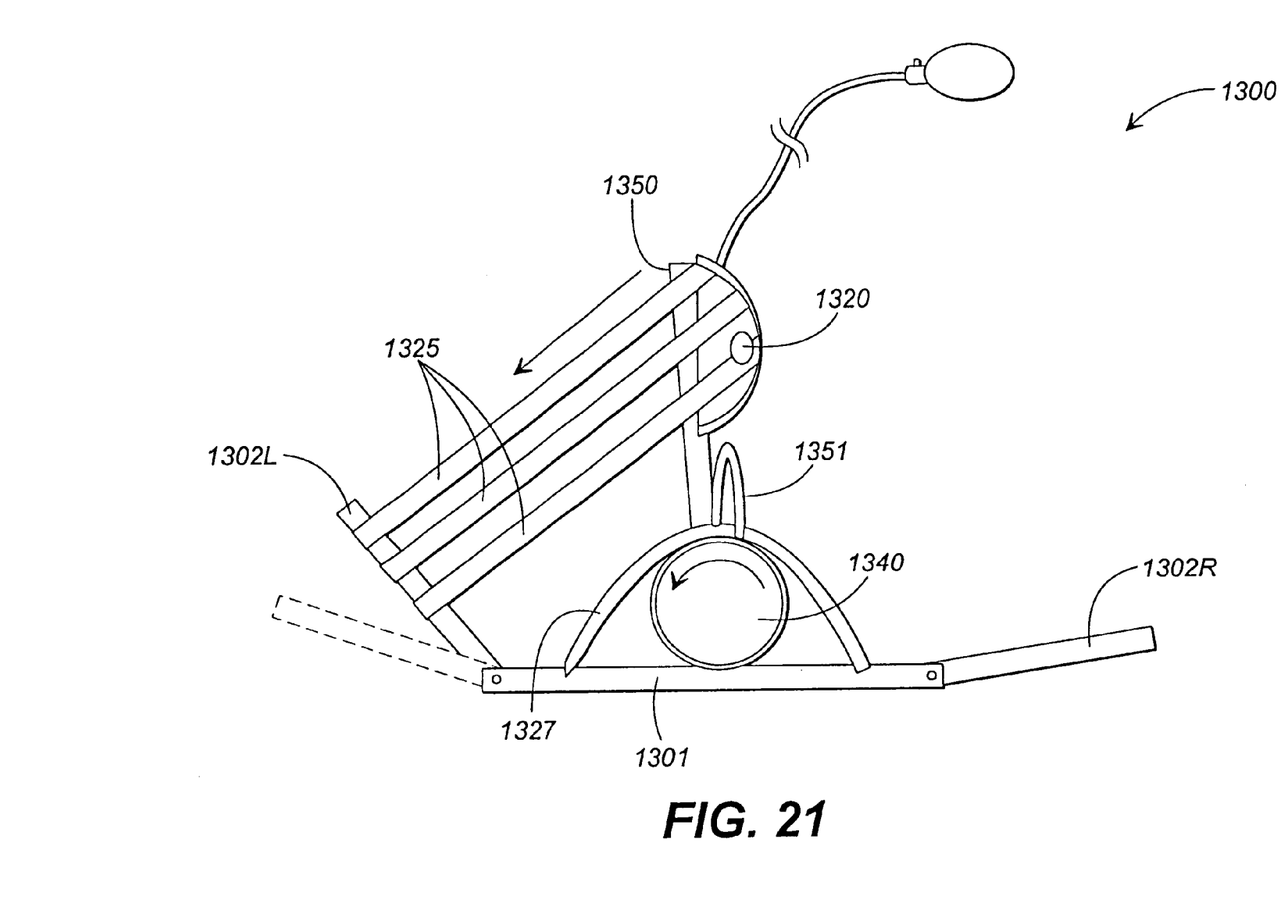

FIGS. 20, 21

FIGS. 20 and 21 are pictorial and end views, respectively, of a forearm supination and pronation device 1300. This device 1300 includes a base 1301, right and left adjustable base flanges 1302L, 1302R, respectively, an inflatable member 1320, straps 1325, a retaining cuff 1327, and a glove assembly 1350 including a thumb retainer 1351.

The base 1302 is configured to be stationary and to provide support for the other members.

The right and left adjustable base flanges 1302L, 1302R, respectively, are configured to the attached to the base, and to be adjustable. During use they are rigidly affixed relative to the base 1302.

The straps 1325 are positioned intermediate one of the base flanges and the rigid post member 1350.

The rigid post member 1350 is attached to the glove assembly 1340. This attachment can be temporary through VELCRO, snaps, or even a clothespin configuration. Alternately the post 1350 could be pivotally attached to the plate 1301.

The glove assembly 1340 can be attached to a user's hand by various means, but the invention contemplates the insertion of the hand into the glove assembly, which is snugged as desired by use of various straps or bands. The glove assembly includes a thumb retainer 1351 perpendicular to the longitudinal axis of the forearm.

By selectively adjusting the flanges and the straps supination and prontation of the forearm may be provided, while the glove twists atop the base plate 1301.

Although a glove assembly is disclosed above, it should be understood that the present invention also contemplates use of the device without a glove assembly. Such contemplation includes the use of some other means for attaching the post to the arm such that the longitudinal axis of the post is substantially parallel to the plane of the palm of the hand. Such an alternate configuration includes a strap which can fit around the hand across the palm and around the back of the hand, or a "clip" which can attach to the hand, or a "thumb sock", which can be used to contain the thumb relative to the post. However, it should be understood that for optimal biomechanical effect the thumb should be oriented generally alongside and parallel to the elongate post.

Options, Variations

It should also be understood that different fluids other, than atmospheric air may be used, such as water, etc. Alternatively, hot or cold fluids, which may provide some therapeutic value, may likewise be used.

Various straps as known in the art may be used in order to maintain the outer boot in place on the wearer's limb.

It should be understood that under an alternative configuration according to the present invention, in order to provide an improved mechanical advantage, a boot may be used with a bent leg (providing an exposed upper horizontal surface) may be used. In such a configuration, the boot would include a strap which would go up and over the top of the knee, which is advantageous especially when providing the dorsitype flexion of the ankle.

It should also be understood that the provision of air to the bladders according the present invention could be provided by automatic means, which may be advantageous in a long term type of treatment, such as the use of periodic inflation and deflation throughout a night time of wearing.

Furthermore, manual inflation and deflation for the provision of specific stretching of tissues may be provided by manual inflation and deflation of one of the bladders.

Finally, it may be understood that is not necessary that two bladders be used during a particular orthotic session; only one bladder may be used if only one type of motion is desired to stretch the limb against muscle tension.

Miscellaneous Comments

As noted above, a structural member may be used to provide structural support for various of the orthotic devices discussed herein. Such a structural device could be made of plastic, wood, metal, a metal/fabric sling, or other material (s) suitable to provide the needed support. It should be noted that although the structural support will need some type of stiffness to provide its support, it does not have to be perfectly rigid; some bending or deflection is possible and may be desirable.

CONCLUSION

Therefore it may be seen that the present invention provides a plurality of devices which provide improvements over known prior art othrotic devices.

While this invention has been described in specific detail with reference to the disclosed embodiments, it will be understood that many variations and modifications may be effected within the spirit and scope of the invention as described in the appended claims.

I claim:

1. An orthotic device for providing motion to a user's limb through movement of a joint, said device comprising:
   a strap;
   an inflatable member connected to said strap and including an inflatable bladder, said inflatable member, when in place, being spaced from said joint and proximate to said limb; and
   a device operatively associated with said inflatable bladder for inflating and deflating said inflatable member such that as said inflatable member is inflated, said strap is placed in increasing tension so as to cause said limb to move partially along the length of said strap and causing said joint to be moved.

2. The device as claimed in claim 1, wherein said inflatable member is configured such that when it is in place, it is in contact with said limb.

3. The device as claimed in claim 1, wherein said strap is elongate and includes two opposing ends and a medial portion therebetween, both of said ends attached to said structural body portion, and said inflatable member attached to said medial portion of said strap such that said inflatable member is captured between said strap medial portion and said limb during said pushing action.

4. An orthotic device for manipulating a user's limb having a joint, said device comprising:
   a structural body portion;
   an inflatable member;
   a flexible strap interconnecting said structural body portion and said inflatable member such that a portion of said limb can be inserted at a location between said structural body portion and said inflatable member and such that said limb portion is in contact with said inflatable member; and
   an inflating device for inflating said inflatable member so that it increases in size, such that as said inflatable member is inflated, said inflatable member tends to push against said limb such that said limb is urged towards said structural body portion in such a manner as to result in flexion or extension of said joint.

5. The device as claimed in claim 4, wherein said inflatable member is attached relative to said flexible strap such that when inflated, said inflatable member urges said limb towards said structural body portion and closes a gap between said limb and said body portion.

6. The device as claimed in claim 4, wherein said strap is elongate and includes two opposing ends and a medial portion therebetween, both of said ends attached to said structural body portion, and said inflatable member attached to said medial portion of said strap such that said inflatable member is captured between said strap medial portion and said limb during said pushing action.

7. An orthotic device for use by a user in combination with an elongate substantially rigid frame member, said device configured for providing movement to a knee joint of a leg of said user and comprising:
   at least one flexible strap having a first end and a second end, said first end configured to be attached to said frame member;
   an inflatable member including an inflatable bladder, said inflatable member being spaced from said knee joint and attached to said second end of said strap such that said leg is positioned between said inflatable member and said frame member when in both above-referenced position, yet while in said first position a gap is present between said knee joint of said user and said frame member; and
   a pump for inflating said inflatable member such that as said inflatable member expands, said flexible strap is placed in tension such that said inflatable member exerts a force against said leg and causes said gap to be reduced upon expansion of said bladder.

8. The device as claimed in claim 7, further comprising an ankle support member attached to said frame member, wherein said leg is captured on one side by said inflatable member and on the other side by said frame member and said ankle support member.

9. The device as claimed in claim 7, wherein said elongate substantially rigid frame member comprises a crutch.

10. The device as claimed in claim 7, further comprising a quick release means for deflating said inflatable member.

11. The device as claimed in claim 7, wherein said strap is elongate and includes two opposing ends and a medial portion therebetween, both of said ends attached to said structural body portion, and said inflatable member attached to said medial portion of said strap such that said inflatable member is captured between said strap medial portion and said limb during said pushing action.

12. A method of adapting an elongate crutch for use by a user in extending a knee joint of a leg having a thigh, said method comprising the steps of:
   A) providing an elongate crutch having an upper and a lower end, said upper end of said crutch configured to be placed under the armpit of a user and said lower end configured to be placed atop a supporting floor surface such that a user may use said crutch as support while walking;
   B) providing a orthotic device for use in conjunction with said crutch, said orthotic device itself comprising:
      1) an inflatable member;
      2) at least one strap; and
      3) a device for inflating and deflating said inflatable member;
   C) positioning said leg adjacent to said crutch in a slightly bent shape such that said leg is generally parallel to said elongate crutch;
   D) attaching said inflatable member relative to said crutch by use of said strap such that said inflatable member is positioned in contact with a portion of said leg and said leg portion is positioned intermediate said crutch and said inflatable member; and
   E) subsequent to step "D", inflating said inflatable member such that said strap is drawn into tension and said inflatable member providing a force atop said leg portion such that said knee joint of said leg moves towards said crutch, and said knee joint also tends to be urged towards a more straight configuration.

13. The method of claim 12, further comprising the step of, prior to step "C", attaching an ankle support member to said crutch, wherein in step "C", said ankle is supported by said ankle support member and said leg is positioned intermediate said inflatable member on one side and said crutch and said ankle support on the opposite side.

14. The method of claim 12, further comprising the step of, prior to step "E", preadjustment of said strap to take up slack in said strap intermediate said crutch and said inflatable member.

15. The method of claim 12, further comprising the step of, subsequent to step "E", deflating said inflatable member.

16. The method of claim 12, wherein in step D, said inflatable member is placed in contact with said thigh of said leg.

17. The method of claim 12, further comprising the step of quickly deflating said inflatable member.

18. An orthotic device for attachment to an arm of a user, said arm having an elbow joint between a forearm and an upper arm, said arm when straight being generally elongate with a first side and a second side, each of said two sides each extending the length of said arm, said device comprising:
   a substantially rigid structural frame portion for contacting said arm at a first location being on said first side of said arm in the vicinity of the elbow;
   an upper arm contacting portion for contacting said upper arm on said second side of said arm, said upper arm contacting portion being attached relative to said body portion;
   an inflatable member for contacting said forearm on said second side of said arm;

at least one strap for attaching said inflatable member relative to said substantially rigid body portion, such that a portion of said forearm is positioned intermediate said substantially rigid body portion and said inflatable member, with a gap being present between said forearm portion and said substantially rigid body portion; and an inflation device for inflating said inflatable member such that said elbow joint tends to be straightened as said forearm pivots relative to and towards said substantially rigid body portion and said gap is at least partially closed.

19. The orthotic device as claimed in claim 18, wherein said inflatable member is in contact with said forearm portion.

20. The orthotic device as claimed in claim 18, wherein said upper arm contacting member is substantially rigid.

21. The orthotic device as claimed in claim 18, wherein said upper arm contacting member is comprised of straps.

22. The orthotic device as claimed in claim 18, wherein said frame portion does not contact said elbow.

23. The orthotic device as claimed in claim 18, wherein said frame portion does contact said elbow.

24. An orthotic device for moving an arm of a user so that external rotation of the shoulder is provided said arm including an upper part, said device comprising:

a strap configured for passing around the chest of said user and for retaining said upper part of said user's arm, such that said upper part of said user's arm is urged towards the side of said user;

an inflatable member for attachment to said strap and for placement intermediate the stomach of the user and the forearm of the user; and a device for inflating said inflatable member such that external rotation of the shoulder is provided.

25. The orthotic device as claimed in claim 24, further comprising a second strap for attaching said inflatable member relative to said user.

26. An orthotic device for moving an arm of a user so that external rotation of the shoulder is provided, said device comprising:

a strap configured for passing around the chest of said user and around said upper part of said user's arm, such that said upper part of said user's arm tends to be retained against the side of said user;

an inflatable member attached to said strap and configured to be positioned against said forarm of said user;

a spacing wedge for use intermediate said inflatable member and the stomach region of said user for spacing purposes such that said forearm of said user and said spacing wedge combine to capture said inflatable member therebwteen; and a device for inflating said inflatable member such that external rotation of the shoulder is provided.

27. The orthotic device as claimed in claim 26, further comprising a second strap for attaching said inflatable member relative to said user.

28. The orthotic device as claimed in claim 27, wherein said spacing wedge is foam.

29. The orthotic device as claimed in claim 27, wherein said spacing wedge is an inflated bag.

30. The orthotic device as claimed in claim 26, wherein said spacing wedge is foam.

31. The orthotic device as claimed in claim 26, wherein said spacing wedge is an inflated bag.

32. A device for providing motion to an ankle of a user, said device comprising:

a base plate member defining an upwardly-directed hole;

an inclined yoke plate, said inclined yoke plate including a yoke configured to fit over the top of said foot, and also defining at least one lower end configured to slidably move within said hole;

a first strap intermediate the upper end of the inclined brace member and said base plate;

an inflatable member for positioning behind the lower leg;

a second strap intermediate and connecting said inclined yoke plate and said inflatable member; and a device for inflating the inflatable member such that said first and second straps are placed in tension and said ankle of said foot is flexed in plantarflexion, and said yoke member at the same time pushes down on said foot to urge it into contact with said plate.

33. The orthotic device as claimed in claim 32, wherein said yoke plate includes an elongate pad within said yoke hole for contact with the upper part of the foot.

34. The orthotic device as claimed in claim 32, wherein said base plate member further includes a spherical member to allow the base plate member to be put on a level supporting surface such as a floor surface such that the spherically shaped member can provide a rolling pivot or rocking point about which the base plate member can rotate.

35. A device for providing motion to an ankle of a user having an associated foot having an associated front part, said device comprising:

A) a structural member, said structural member itself comprising; a slipper portion for accepting said front part of said foot; and a vertical flange portion extending upwardly from said slipper portion;

B) an inflatable member for positioning behind the lower leg;

C) a strap intermediate said inflatable member and said vertical flange portion; and D) a device for inflating the inflatable member such that said strap is placed in tension and said ankle of said foot is flexed in plantarflexion.

36. The device as claimed in claim 35, wherein said structural member further includes a spherical member to allow the structural member to be put on a level supporting surface such as a floor surface such that the spherically shaped member can provide a rolling pivot or rocking point about which the structural member can rotate.

37. A device for providing motion to an ankle of a leg of a user, said device comprising:

a base frame member;

a foot supporting member attached to said base for supporting the foot proximate the toes;

a cuff for containing said leg;

an inflatable member for positioning on the anterior aspect of the distal thigh with the knee flexed to a minimum of 90 degrees;

a strap intermediate said inflatable member and said base frame member;

a device for inflating the inflatable member such that said strap is placed in tension, said inflatable member pushes down on said knee, said cuff contains said leg while allowing said leg to slide within and relative to said cuff, and said ankle is flexed in dorsiflexion.

38. A forearm supination device for use with a user having a forearm having at one end a hand defining a palm, said device comprising:

a base including a base portion;

an elongate post member;

a device for attaching said post member to said hand of the user such that the longitudinal axis of the post is substantially parallel to the plane of the palm of the hand and perpendicular to the longitudinal axis of the forearm;

an inflatable member attached to said post member opposite said base portion; at least one strap between said inflatable member and said base portion; and an air pump to cause said inflatable member to inflate and said strap to go into tension, causing forearm supination and pronation.

39. The forearm supination device as claimed in claim 38, further comprising a glove to provide said attachment between said post member and said hand of said user.

40. The forearm supination device as claimed in claim 38, wherein said post member is pivotably attached relative to said base at a location distant from said base portion.

41. An orthotic device for moving an arm of a user so that external rotation of the shoulder is provided, said device comprising:

a strap for passing around the chest of said user and around said upper part of said user's arm, such that said upper part of said user's arm is urged towards the side of said user;

an inflatable, member attached to said strap;

a foam spacing wedge for use intermediate said inflatable member and the stomach region of said user for spacing purposes such that said forearm of said user and said spacing wedge combine to capture said inflatable member there between; and a device for inflating said inflatable member such that external rotation of the shoulder is provided.

42. An orthotic device for moving an arm of a user so that external rotation of the shoulder is provided, said device comprising:

a strap for passing around the chest of said user and around said upper part of said user's arm, such that said upper part of said user's arm is urged towards the side of said user;

an inflatable member attached to said strap;

a spacing wedge, comprised of an inflated bag, for use intermediate said inflatable member and the stomach region of said user for spacing purposes such that said forearm of said user and said spacing wedge combine to capture said spacing wedge therebetween; and a device for inflating said inflatable member such that external rotation of the shoulder is provided.

43. An orthotic device for moving an arm of a user so that abduction of the shoulder is provided, said device comprising:

a chest strap for passing around the chest of said user;

a spacing wedge attached to said strap for positioning underneath the armpit of said user;

an inflatable member attached to said spacing wedge for positioning between said spacing wedge and the upper arm of said user;

a shoulder-to-crotch strap attached to said chest strap, for extending to underneath the groin region or said user in order to provide support for pulling the scapula downwardly, thus tending to isolate motion to the glenohumeral joint;

a device for inflating said inflatable member such that external rotation of the shoulder is provided while said shoulder-to-crotch strap tends to isolate motion to the glenohumeral joint.

44. A method of using an elongate structural member for use by a user in extending a knee joint of a leg having a thigh, said method comprising the steps of:

A) providing an elongate structural member having an upper and a lower end;

B) providing a orthotic device for use in conjunction with said elongate structural member, said orthotic device itself comprising:
  1) an inflatable member;
  2) at least one strap; and
  3) a device for inflating and deflating said inflatable member;

C) positioning said leg adjacent to said elongate structural member in a slightly bent shape such that said leg is generally parallel to said elongate structural member;

D) attaching said inflatable member relative to said elongate structural member by use of said strap such that said inflatable member is positioned in contact with a portion of said leg and said leg portion is positioned intermediate said elongate structural member and said inflatable member; and E) subsequent to step "D", inflating said inflatable member such that said strap is drawn into tension and said inflatable member providing a force atop said leg portion such that said knee joint of said leg moves towards said elongate structural member, and said knee joint also tends to be urged towards a more straight configuration.

* * * * *